United States Patent [19]

Grey

[11] Patent Number: 4,533,754
[45] Date of Patent: Aug. 6, 1985

[54] PREPARATION OF ALDEHYDES FROM ARYL ACID HALIDES AND ORGANOZINC COMPOUNDS WITH COMPLEX PALLADIUM CATALYSTS

[75] Inventor: Roger A. Grey, West Chester, Pa.

[73] Assignee: Atlantic Richfield Company, Los Angeles, Calif.

[21] Appl. No.: 633,546

[22] Filed: Jul. 23, 1984

[51] Int. Cl.³ .................................................. C07C 45/00
[52] U.S. Cl. ..................... 568/437; 568/316; 568/424; 260/465 R; 564/169
[58] Field of Search ............... 568/437, 424, 316; 260/465 R; 564/169

[56] References Cited

U.S. PATENT DOCUMENTS 3,277,178 10/1966 Brown .................... 568/437 X
3,517,066 6/1970 Gurien et al. .............. 568/437
4,036,877 7/1977 Petro et al. .............. 568/437 X
4,211,727 7/1980 Entwistle ................. 568/437

*Primary Examiner*—Bernard Helfin
*Attorney, Agent, or Firm*—Delbert E. McCaslin

[57] ABSTRACT

A process for the preparation of aldehydes of the formula

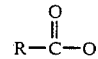

wherein R is a substituted or unsubstituted aryl group containing one or more benzenoid rings which comprises reacting an aryl acid halide with an organozinc compound in solvent in the presence of a palladium metal complex catalyst.

18 Claims, No Drawings

PREPARATION OF ALDEHYDES FROM ARYL ACID HALIDES AND ORGANOZINC COMPOUNDS WITH COMPLEX PALLADIUM CATALYSTS

BACKGROUND OF THE INVENTION

This invention relates to a process for the preparation of aldehydes by the reaction of organic acid halides with organozinc compounds. The resulting aldehydes are useful as starting materials for the production of pharmaceuticals, flavoring compounds, photographic chemicals and dyes as well as in soaps and perfumery.

The invention relates more specifically to the reaction of an aryl acid halide with a straight or branched chain alkylzinc compound in a solvent in the presence of a complex palladium catalyst selected from $(Ph_3P)_2PdCH_2Ph(Cl)$ which is chlorobenzyl bis-triphenylphosphine palladium, $(Ph_3As)_4Pd$ which is tetrakis-triphenylarsine palladium or $(Ph_3P)_4Pd$ which is tetrakis-triphenylphosphine palladium.

Applicant is not aware of any truly pertinent art that is deemed to be anticipatory or suggestive of the concept of the present invention.

It is an object of this invention to provide a process for the preparation of aldehydes employing certain complex palladium catalysts.

It is a further object of the present invention to prepare aldehydes in high yield and selectivities by reacting aryl acid halides with alkylzinc compounds in a solvent in the presence of specific complex catalysts.

These and other objects and advantages of this invention will become apparent from the description of the invention which follows and from the claims.

BRIEF DESCRIPTION OF THE INVENTION

The present invention comprises a process for the preparation of aldehydes, such as benzaldehyde, by reacting an aryl acid halide, such as benzoyl chloride with an alkylzinc compound such as di-n-butylzinc in a solvent such as a diethylether or n-hexane or a mixture thereof at temperatures of from $-78°$ C. to $200°$ C. in the presence of a palladium metal complex catalyst selected from $(Ph_3P)_2PdCH_2Ph(Cl)$, $(Ph_3As)_4Pd$ or $(Ph_3P)_4Pd$.

DETAILED DESCRIPTION OF THE INVENTION

In accordance with the present invention, aldehydes are produced by a complex palladium metal catalyzed reaction of organic acid halides of the general formula

wherein R is a substituted or unsubstituted aryl group containing one or more benzenoid rings which may be fused or joined by single valency bonds, said substituents being selected from halides, alkyl, aryl, nitro, cyano, amido, keto or alkoxy groups and X is a halide with an organozinc compound of the formula $(R')_2Zn$ or $R'ZnX$ wherein $R'$ is a straight or branched chain alkyl group containing from 2 to 20 carbon atoms and X is a halide. The reaction is carried out in solvent at temperatures which may range from about $-78°$ C. to about $200°$ C. and preferably are carried out between $0°$ C. and $66°$ C. and more preferably between $15°$ C. and $35°$ C.

The reaction may be carried out in any suitable reactor which is equipped with a means for addition of reactants and catalyst, a means for agitation, and a means for regulating temperature. Although the order of addition of reactants, solvent and catalyst components may vary, a general procedure for carrying out the reaction is to charge the alkylzinc compound, complex catalyst and the aryl acid chloride along with the solvent into the reaction vessel at atmospheric pressure with stirring and regulation of the temperature until the reaction is complete. The reaction can be carried out batchwise, semicontinuous, or as a continuous process. The reaction products are recovered and treated by any conventional method, such as fractionation, distillation, extraction etc. to effect separation of the aldehyde from any unreacted material, catalyst and by-products.

The aryl acid halides employed as reactants in the process of the present invention conform to the general formula

wherein R is as hereinabove described and X is a halide. R may be unsubstituted or substituted with halide, alkyl, aryl, nitro, cyano, amido, keto or alkoxy groups which do not interfere with the reaction. Representative aryl acid halides suitable for use in this invention include, for example, benzoyl bromide, benzoyl chloride, benzoyl fluoride, terephthaloyl chloride, terephthaloyl bromide, α or β naphthoyl bromide, α or β naphthoyl chloride, cinnamoyl chloride, cinnamoyl bromide and the like.

The organozinc compounds employed as reactants in the process of the invention conform to the general formulae $(R')_2 Zn$ or $R'ZnX$ wherein $R'$ is a substituted or unsubstituted straight or branched chain alkyl group having from 2 to 20 carbon atoms, preferably 2–6 carbon atoms, and X is a halide. $R'$ may be substituted with alkyl, aryl, nitro, cyano, amido, keto or alkoxy radicals provided there is a β hydrogen present to form the aldehyde and which do not interfere with the reaction. Representative organozinc compounds as hereinabove described for use in this invention include, for example, di-n-butylzinc, di-n-propylzinc, diisopropylzinc, butylzinc chloride, butylzinc bromide, propylzinc chloride, diethylzinc, ethylzinc bromide, and the like.

Aldehyde products which may be prepared by the process of this invention include, for example, benzaldehyde tolylaldehyde, anisaldehyde, 4-chlorobenzaldehyde, p-nitrobenzaldehyde, and the like.

The palladium metal complex catalysts which are employed in the process of this invention at a molar ratio of aryl acid chloride to complex catalyst of from about 1:1 to $1:10^{-6}$ and preferably from 100:1 to 5000:1 are selected $(Ph_3P)_2PdCH_2Ph(Cl)$, $(Ph_3As)_4Pd$ or $(Ph_3P)_4Pd$. With these particular complex palladium catalysts, aryl aldehydes are produced in high yield and selectivities.

The reaction of the present invention is carried out in a non-reactive solvent or a mixture of solvents in which the reactant aryl acid chloride, organozinc compound and complex palladium catalyst are essentially soluble. The amount of solvent used will generally be about 50% by weight based on the reaction mixture however, lesser or greater amounts may be employed depending on the particular reactants and viscosity of the mixture. Suitable solvents include for example ethers such as tetrahydrofuran, diethylether, dioxane, diphenylether, diethyleneglycol dimethylether, triethyleneglycol dimethyl ether, 1,2-dimethoxyethane and the like, alkanes such as n-pentane, isopentane, n-hexane, 2-methylpentane, n-heptane, cyclopentane, cyclohexane, methylcyclohexane and the like, aromatic hydrocarbons such as toluene, benzene, xylene, nitrobenzene, nitrotoluene and the like. The ether solvents or mixtures of ether solvents with other solvents such as the aromatic hydrocarbons are preferred.

A general postulated equation for the reaction of the present invention may be represented as follows:

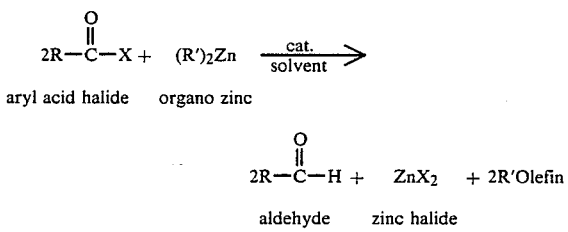

wherein R, R' and X are as hereinabove described. A wide variety of aldehydes can be prepared by the process of this invention.

As indicated hereinabove, the reaction will proceed at temperatures of from about −78° C. to 200° C. It is generally preferred to operate the process at temperatures of from about 0° C. to 66° C. and more preferably at temperatures of from 15° C. to 35° C. to obtain a convenient rate of reaction. The reaction temperature will depend on the particular aldehyde being synthesized including the reactants employed.

The process of the present invention is generally carried out at atmospheric pressure although higher pressures at the higher reaction temperatures or lower pressures may be employed, if desired.

The reaction time is generally dependent on the aldehyde being produced, the reaction temperature and the catalyst employed, and will vary depending on whether the process is continuous or batch but will generally range between about 1 to 10 hours.

The following Examples are provided to illustrate the invention in accordance with the principles of this invention, but are not to be construed as limiting the invention in any way except as indicated by the appended claims.

EXAMPLE 1

PREPARATION OF BENZALDEHYDE

The preparation of benzaldehyde was carried out in an argon atmosphere with anhydrous reagents using standard inert gas techniques. Water was removed from zinc chloride by heating at 150° C. under vacuum (0.5 mm of mercury (Hg)). Tetrahydrofuran (THF) was dried by distillation under argon from lithium aluminum hydride. The catalyst, chlorobenzyl bis-triphenylphosphine palladium was prepared according to the literature procedure (P. Fitton, J. E. McKeon and B. C. Ream, *Chem. Commun.*, 370–371 (1969) by the reaction of benzyl chloride and tetrakistriphenylphosphine palladium. The isolated metal complex was not recrystallized. Di-n-butylzinc reactant was prepared in situ from zinc chloride and n-butylmagnesium chloride as described below.

A five liter, four neck, fluted flask equipped with a mechanical stirrer was charged with 118 grams (0.86 mol) of zinc chloride and 1.2 liter of tetrahydrofuran. This solution was cooled to 0° C. and 800 ml (1.6 mol) of n-butylmagnesium chloride (Grignard Reagent) was added via an addition funnel over a 2 hour period. The reaction mixture was stirred at room temperature for 2 hours to insure complete conversion to di-n-butylzinc containing 2 equivalents of MgCl$_2$ in solution as by-product which was not removed.

The above di-n-butylzinc slurry containing a white precipitate was cooled to 0° C. and 1.1 gram (0.0014 mol) of chlorobenzyl bis-triphenylphosphine palladium added as a solid. To this mixture, 240 grams (1.7 mol) of benzoyl chloride in 200 ml of THF was added over a 1 hour period. The reaction mixture was stirred in an ice bath for 2 additional hours at 0° C. and at 23° C. for 2 hours in an oil bath to insure complete reaction. The reaction mixture was cooled in an ice bath to 0° C. and a 3N HCl solution added at a rate to maintain the temperature below 16° C. until all of the white (ZnCl$_2$) precipitate dissolved (∼800 ml of acid solution was required). The aqueous layer was separated and the organic layer washed with 100 ml portions of water and brine. The combined aqueous layers were extracted with 500 ml of diethyl ether which was then washed with water and brine. The combined organic layers were dried over magnesium sulfate, filtered and the solvent removed under reduced pressure. The volatiles were flash distilled away from the catalyst residue and other solids at 65° C. and 0.5 mm of Hg. The resulting clear distillate was fractionally distilled using a 20 cm vigreaux column at 10 cm of Hg. The fraction boiling between 100° C. and 104° C. (79 g, 0.75 mol) by G. C. (gas chromatographic) analysis showed greater than 99% purity benzaldehyde (6 ft. glass column packed with 10% sp 2100, 80° to 300° C. at 10° C min). This represents a 44% yield based on the Grignard Reagent.

EXAMPLES 2-12

In Examples 2-12 which follow in table form, the procedure of Example 1 was repeated using the various catalysts, aryl acid halides and organozinc compounds. The entries for R, R' and X refer to the following equation.

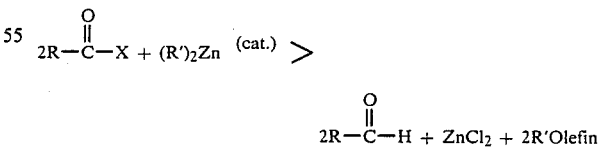

TABLE

| | ALDEHYDE SYNTHESIS[a] | | | | | | | |
|---|---|---|---|---|---|---|---|---|
| Example No. | R | X | R' | Catalyst | Product | Solvent[d] | Time (hours)[c] | Yield[b] |
| 2 | Phenyl | Cl | n-C$_4$H$_9$ | none | benzaldehyde | THF/Et$_2$0 | 2 | 0 |
| 3 | Phenyl | Cl | C$_2$H$_5$ | (Ph$_3$P)$_2$PdCH$_2$Ph(Cl) | benzaldehyde | THF | 2 | 60 |
| 4 | Phenyl | Cl | C$_2$H$_5$ | (Ph$_3$P)$_2$PdCH$_2$Ph(Cl) | benzaldehyde | dioxane | 5 | 36 |

TABLE-continued
ALDEHYDE SYNTHESIS[a]

| Example No. | R | X | R' | Catalyst | Product | Solvent[d] | Time (hours)[c] | Yield[b] |
|---|---|---|---|---|---|---|---|---|
| 5 | Phenyl | Cl | $C_2H_5$ | $(Ph_3As)_4Pd$ | benzaldehyde | THF | 2 | 36 |
| 6 | Phenyl | Cl | $n\text{-}C_4H_9$ | $(Ph_3P)_4Pd$ | benzaldehyde | $THF/Et_2O$ | 2 | 46 |
| 7 |  | Cl | $C_2H_5$ | $(Ph_3P)_2PdCH_2Ph(Cl)$ | tolylaldehyde | THF | 2 | 41 |
| 8 | $CH_3O$-⟨O⟩- | Cl | $C_2H_5$ | $(Ph_3P)_2PdCH_2Ph(Cl)$ | anisaldehyde | THF | 2 | 45 |
| 9 |  | Cl | $C_2H_5$ | $(Ph_3P)_2PdCH_2Ph(Cl)$ | 4-chlorobenzaldehyde | THF | 2 | 36 |
| 10 | Phenyl | Br | $C_2H_5$ | $(Ph_3P)_2PdCH_2Ph(Cl)$ | benzaldehyde | THF | 2 | 55 |
| 11 | Phenyl | I | $C_2H_5$ | $(Ph_3P)_2PdCH_2Ph(Cl)$ | benzaldehyde | THF | 2 | 52 |
| 12 | Phenyl | F | $C_2H_5$ | $(Ph_3P)_2PdCH_2Ph(Cl)$ | benzaldehyde | THF | 2 | 46 |
| 13 | Phenyl | Br | $n\text{-}C_4H_9$ | $(Ph_3P)_2PdCH_2Ph(Cl)$ | benzaldehyde | THF/Toluene | 2 | 43 |
| 14 | Phenyl | Cl | $n\text{-}C_4H_9$ | $(Ph_3P)_2PdCH_2Ph(Cl)$ | benzaldehyde | THF/hexane | 2 | 40 |

[a]Conditions: Acid Halide = 11 mmol, Grignard Reagent = 10 mmol, $ZnCl_2$ = 5.4 mmol, solvent = 20 ml, catalyst = 0.03 mmol.
[b]GC (Gas Chromatograph) yields based on mmol of Grignard reagent used to prepare organozinc (internal standard = hexadecane).
[c]Indicates time a 23° C. In each Example the acid halide was added to zinc reagent containing the catalyst at 0° C. for ½ hour before warming to 23° C.
[d]THF/diethylether and THF/n-hexane ratio was 4:1.

I claim:

1. A process for the preparation of an aldehyde of the formula $$R-\overset{O}{\underset{\|}{C}}-H$$

wherein R is a substituted or unsubstituted aryl group containing one or more benzenoid rings which may be fused or joined by single valency bonds, said substituents being selected from halides, alkyl, aryl, nitro, cyano, amido, keto or alkoxy groups, which comprises reacting in a solvent at a temperature of from about −78° C. to 200° C., an organic acid halide of the formula $$R-\overset{O}{\underset{\|}{C}}-X$$

wherein R is as hereinabove described, and X is a halide, with an organozinc compound of the formula $(R')_2Zn$ or $R'ZnX$ wherein R' is a straight or branched chain alkyl group containing from 2 to 20 carbon atoms and X is a halide, in the presence of a palladium metal complex catalyst selected from $(Ph_3P)_2PdCH_2Ph(Cl)$, $(Ph_3As)_4Pd$ or $(Ph_3P)_4Pd$.

2. A process according to claim 1 wherein the organic acid halide is an organic acid chloride.

3. A process according to claim 2 wherein the organic acid chloride is benzoyl chloride.

4. A process according to claim 1 wherein the organozinc compound is selected from di-n-butylzinc or diethylzinc.

5. A process according to claim 1 wherein the catalyst is employed at a molar ratio of aryl acid halide to catalyst of from about 1:1 to $1:10^{-6}$.

6. A process according to claim 5 wherein the molar ratio is in the range of from 100:1 to 5000:1.

7. A process according to claim 1 wherein the catalyst is chlorobenzyl bis-triphenylphosphine palladium.

8. A process according to claim 1 wherein the solvent is an ether.

9. A process according to claim 8 wherein the solvent is selected from tetrahydrofuran, diethylether or a mixture of tetrahydrofuran and diethylether.

10. A process according to claim 9 wherein the solvent is a mixture of 4 parts tetrahydrofuran to 1 part diethylether.

11. A process according to claim 1 wherein the solvent is a mixture of 4 parts tetrahydrofuran to 1 part hexane.

12. A process according to claim 1 wherein the temperature is between 0° C. and 66° C.

13. A process according to claim 12 wherein the temperature is between 15° C. and 35° C.

14. A process for the preparation of benzaldehyde which comprises reacting in an ether solvent at a temperature of from about 0° C. to 66° C., a benzoyl halide with an organozinc compound of the formula $(R')_2Zn$ wherein R' is a straight or branched chain alkyl group containing from 2 to 20 carbon atoms in the presence of a catalytic amount of chlorobenzyl bis-triphenylphosphine palladium.

15. A process according to claim 14 wherein the ether solvent is tetrahydrofuran.

16. A process according to claim 14 wherein the benzoyl halide is benzoylchloride.

17. A process according to claim 14 wherein the organozinc compound is di-n-butylzinc.

18. A process according to claim 14 wherein the organozinc compound is diethylzinc.

* * * * *